(12) United States Patent
Anderson et al.

(10) Patent No.: US 6,298,874 B1
(45) Date of Patent: Oct. 9, 2001

(54) SLAB GEL PROCESSING TANK

(75) Inventors: Norman G. Anderson, Rockville, MD (US); N. Leigh Anderson, Washington, DC (US)

(73) Assignee: Large Scale Proteomics Corporation, Rockville, MD (US)

( * ) Notice: Subject to any disclaimer, the term of this patent is extended or adjusted under 35 U.S.C. 154(b) by 0 days.

(21) Appl. No.: 09/504,493

(22) Filed: Feb. 15, 2000

(51) Int. Cl.⁷ ....................................................... C25B 7/00
(52) U.S. Cl. ............................................. 137/558; 204/619
(58) Field of Search ................. 137/558; 204/618, 204/619, 626

(56) References Cited

U.S. PATENT DOCUMENTS

| | | |
|---|---|---|
| D. 315,951 | 4/1991 | Berninger et al. . |
| 3,888,758 | 6/1975 | Saeed . |
| 4,574,040 | 3/1986 | Delony et al. . |
| 4,594,064 * | 6/1986 | Anderson .................... 204/619 X |
| 4,772,373 | 9/1988 | Ebata et al. . |
| 4,773,984 | 9/1988 | Flesher et al. . |
| 4,830,725 * | 5/1989 | Berninger et al. ............ 204/620 |
| 5,073,246 | 12/1991 | Chu et al. . |
| 5,344,534 * | 9/1994 | Danziger .................... 204/618 X |
| 5,449,446 * | 9/1995 | Verma et al. ............... 204/620 X |
| 5,458,749 | 10/1995 | Stone et al. . |
| 5,792,332 * | 8/1998 | Montecino et al. ............ 204/618 |
| 5,993,628 * | 11/1999 | Selby et al. ................ 204/620 X |
| 6,090,255 * | 7/2000 | Riley et al. ................ 204/618 X |

* cited by examiner

*Primary Examiner*—John Rivell
(74) *Attorney, Agent, or Firm*—Roylance, Abrams, Berdo & Goodman, L.L.P.

(57) ABSTRACT

A slab gel processing tank is provided according to the invention. The slab gel processing tank comprises a bottom, two substantially parallel end panels, and two substantially parallel side panels having substantially vertical lower portions and outwardly angled upper portions, with the upper portions being textured to minimize contact with a gel slab, wherein the tank is adapted to be filled with a gel processing working fluid.

32 Claims, 3 Drawing Sheets

SLAB GEL PROCESSING TANK

BACKGROUND OF THE INVENTION

1. Field of the Invention

The present invention relates generally to an electrophoresis gel processing apparatus.

2. Description of the Background Art

Gel electrophoresis is a process for distinguishing and identifying organic macromolecules. Some of the uses of gel electrophoresis are protein analysis and DNA analysis. Gel electrophoresis typically separates macromolecule components in one or two dimensions to provide a result wherein individual macromolecule components appear as bands or spots. The bands or spots may be analyzed to determine the abundance and characteristic of macromolecule components.

Humans possess a staggering number of such macromolecules whose functions and locations await discovery. In response to this challenge, a wide variety of processes and equipment systems have been developed to augment and speed up the gel electrophoresis process through large-scale automation.

Gel electrophoresis is so called because a gel medium (typically a polyacrylamide gel) is used in the process. Sample macromolecules to be analyzed are typically applied to a surface or edge of the gel. The gel is subjected to an electric field (the process of electrophoresis) and the applied macromolecules (which are generally electrically charged) move through the gel medium, yielding a physical separation of the component macromolecules.

There are different types of electrophoresis gels, with one type being a slab (or sheet), typically one to two millimeters thick and roughly the size of a sheet of paper. The gel slab is soft, rubbery, and pliable.

Slab gels may be used alone, or as the second dimension of a two-dimensional separations procedure. In the first dimension of a two-dimensional separation, a first dimension isoelectric focusing separation is performed in which proteins of a test sample are separated through a noodle-like gel strand under the influence of an electric field. As a result, the macromolecule components in the test sample are physically separated in one dimension on the basis of their electrical charges.

In the second dimension electrophoresis step of a two-dimensional electrophoresis process, the first dimension gel strand is placed on an edge of a two-dimensional gel slab (or sheet). The slab and first dimension gel strand are then subjected to electrophoresis to cause the macromolecule components to migrate through the electrophoresis gel slab. As a result of this second electrophoresis, the macromolecule components travel through the gel slab at different rates and are separated on the basis of polypeptide chain length (roughly proportional to molecular weight). The macromolecule components are therefore separated in two dimensions.

After electrophoresis, the gel slab must still be processed so that the identities, relative positions, and concentrations of macromolecule components may be determined. This may include treatment with fixatives, stains, developers, and washes. The gel may need to be submerged multiple times in such solutions, and this must be done in a controllable environment, without damage to the gel.

There remains a need in the art, therefore, for improvements in electrophoresis gel processing apparatus.

SUMMARY OF THE INVENTION

A slab gel processing tank is provided according to a first aspect of the invention. The slab gel processing tank comprises a bottom, two substantially parallel end panels, and two substantially parallel side panels having substantially vertical lower portions and outwardly angled upper portions, with the upper portions including a textured surface to minimize contact with a gel slab, wherein the tank is adapted to be filled with a gel processing working fluid.

A slab gel processing tank is provided according to a second aspect of the invention. The slab gel processing tank comprises a bottom, two substantially parallel end panels, two substantially parallel transparent side panels having substantially vertical lower portions and outwardly angled upper portions, with the upper portions including a textured surface with a plurality of ridges and troughs adapted to minimize contact with a gel slab, the plurality of ridges and troughs having a substantially pyramidal shape, a fluid level sensor, a drain, and an input, wherein the tank is adapted to be filled with a gel processing working fluid.

A method for decreasing a contact area between a slab of substantially planar gel material and a solid support is provided according to a third aspect of the invention. The method includes the step of providing a gel-contacting surface of the solid support with a plurality of projections, wherein the plurality of projections touch the gel and decrease an actual contact area between the gel and the support.

The above and other features and advantages of the present invention will be further understood from the following description of the preferred embodiments thereof, taken in conjunction with the accompanying drawings.

DETAILED DESCRIPTION OF THE PREFERRED EMBODIMENTS

Figure 1:
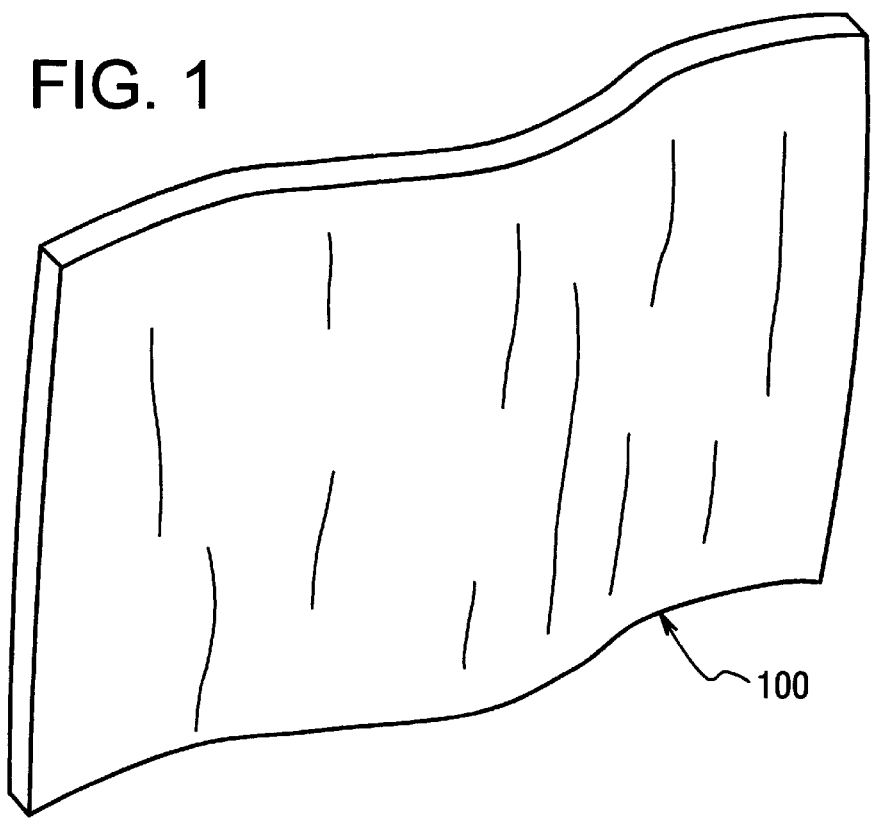
FIG. 1 shows a slab electrophoresis gel.

FIG. 1 shows a slab electrophoresis gel 100 as is commonly used in an electrophoresis analysis: a slab-like, or sheet-like piece of flexible material. As part of the development of the gel slab 100 after electrophoresis, the gel slab 100 may need to be stained and otherwise processed by immersion in fixatives, stains, developers, washes, etc.

Figure 2:
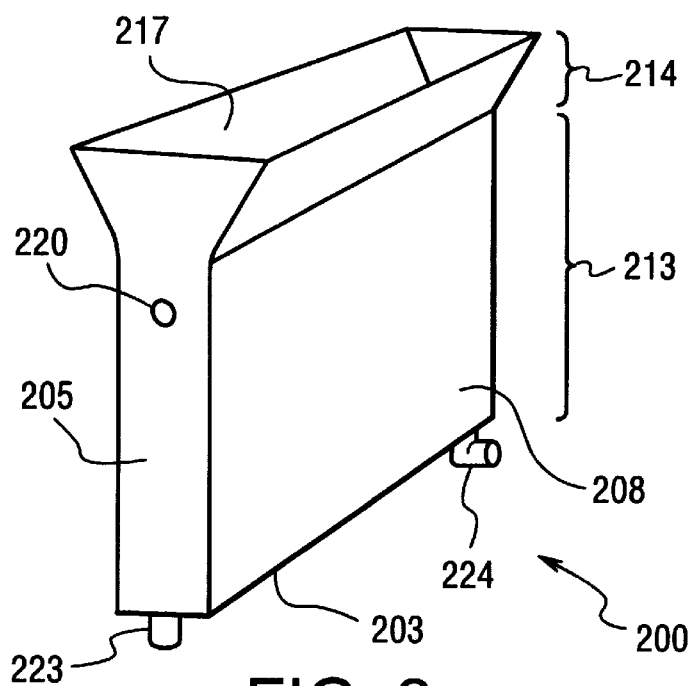
FIG. 2 shows one embodiment of the gel processing tank of the present invention.

FIG. 2 shows one embodiment of the gel processing tank 200 of the present invention. The tank 200 includes a bottom 203, two substantially parallel end panels 205, and two substantially parallel side panels 208.

In the preferred embodiment, the two substantially parallel side panels 208 are about one inch apart, giving the tank 200 a sufficient interior volume to hold a gel 100 but without requiring the use of excessive working fluid.

The side panels 208 further include lower portions 213 and upper portions 214. The lower portions 213 are substantially vertical while the upper portions 214 slope outwardly. The lower portions 213 of the side panels 208 are preferably transparent so that when the gel 100 is placed in the tank 200 it may be visible through the lower portions 213 of the tank 200. In addition, the transparent lower portions 213 may allow the gel 100 to be scanned, photographed or otherwise converted into an image while suspended in the tank 200.

The upper portions 214 are sloped so that when the gel 100 is being lowered into the tank 200 it is progressively guided into the main body (i.e., lower portion 213) of the tank 200. The tank 200 may include a textured surface 217 on the inner sloping surfaces of the upper portions 214. The purpose of the textured surface 217 is to prevent the gel 100 from sticking to or being hung up on the sides of the tank 200. Because the gel 100 is rather soft and rubbery, it tends to stick to the tank 200 when it comes into contact with it. Due to the fact that the gel may be somewhat wet, there may be some capillary action (i.e., an attraction) between the gel 100 and the tank 200. The textured surface 217 therefore minimizes contact between the tank 200 and the gel 100 and minimizes any capillary action.

Figure 3:
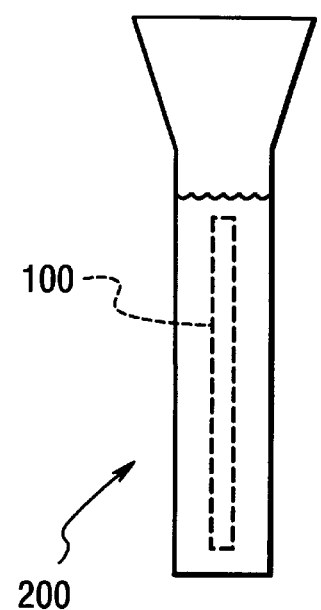
FIG. 3 shows a gel in position in the tank.

The tank 200 may additionally include an input conduit 223, an output conduit 224, and a fluid level sensor 220. In use, the tank 200 may be filled with a working fluid through the input conduit 223. The working fluid may be a fluid such as a stain or dye mixture, a wash or developer, a fixative, etc., and the gel 100 may be lowered into and immersed in the working fluid. The fluid level sensor 220 may be used to both fill the tank 200 and also to maintain a working fluid level as the gel 100 is lowered into the tank 200. This is shown in FIG. 3. At the end of a stain, developer, or wash cycle, the particular working fluid may be removed through the output conduit 224.

In addition to use as a sloping sidewall in the tank 200 (i.e., upper portion 214), the textured surface 217 may be used as a solid support. The textured surface 217 may be an inclined or horizontal surface on which the gel 100 may be placed. Due to the decreased friction and attraction, the gel 100 may be pulled across or otherwise moved on the textured surface 217. As described and shown below with FIGS. 4A–4B and FIGS. 5A–5B, the textured surface 217 may contain a plurality of projections so that contact between the gel 100 and the textured surface 217 is decreased.

Figure 4A:
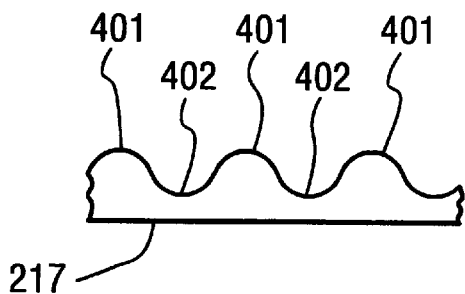
FIGS. 4A–4G show several different embodiments of a textured surface on outwardly sloped upper portions of the side panels.
Figure 4B:
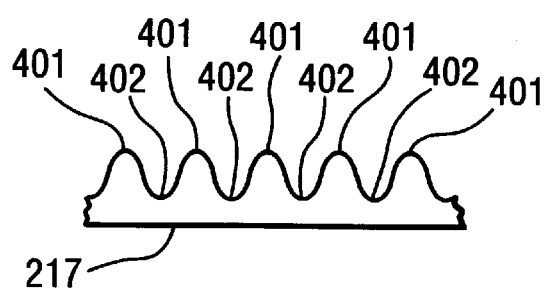
Figure 4C:
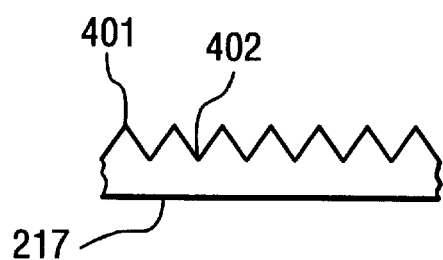
Figure 4D:
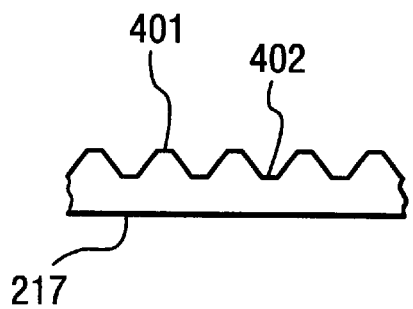

FIGS. 4A through 4G show several different embodiments of the textured surface 217. FIG. 4A shows a textured surface 217 formed of a plurality of ridges 401 and troughs 402. Each embodiment as shown in FIGS. 4A–4D contain a plurality of ridges 401 and troughs 402, as shown in FIG. 5A. The ridges 401 and troughs 402 in this embodiment are substantially circular in cross-sectional shape. In the embodiment of FIG. 4B, the ridges 401 and troughs 402 are substantially sinusoidal in cross-section. In the embodiment of FIG. 4C, the ridges 401 and troughs 402 are substantially triangular in cross-section. In the embodiment of FIG. 4D, the ridges 401 and troughs 402 are substantially triangular in cross-section, but with squared-off peaks 401 and valleys 402.

Figure 4E:
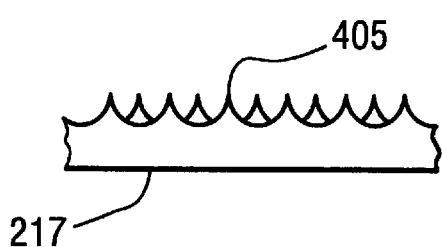
Figure 5A:
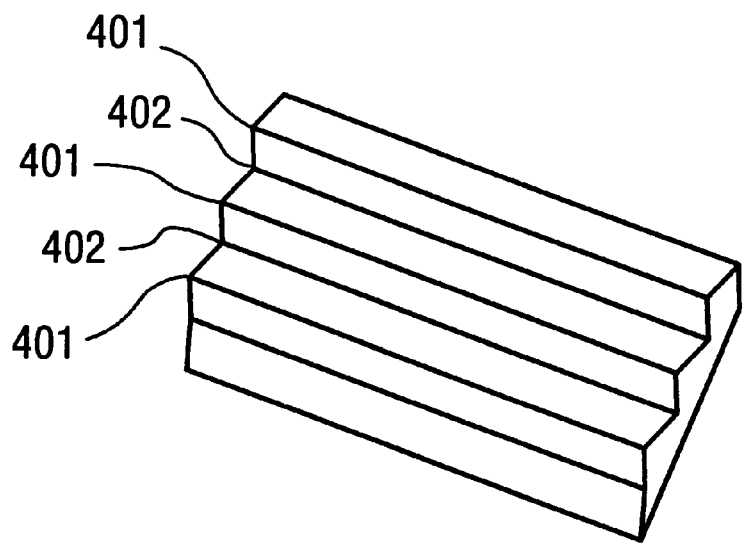
FIGS. 5A–5B show textured surface embodiments having ridges and individual peaks.
Figure 5B:
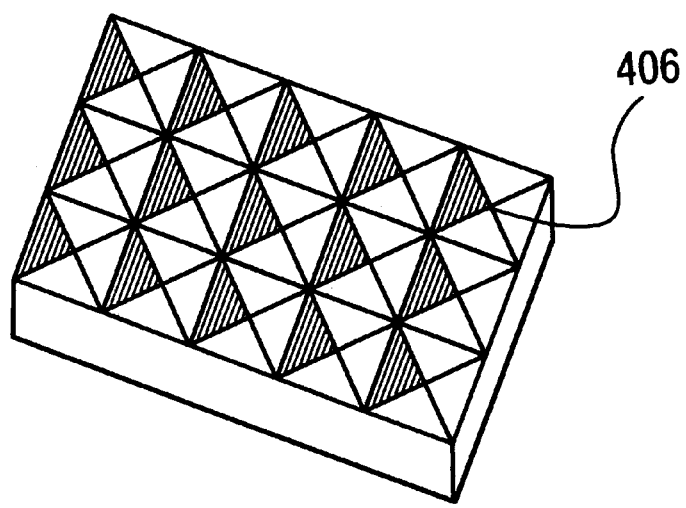

FIGS. 4E–4D show embodiments wherein the ridges 401 and troughs 402 are replaced by individual peaks 405–407. FIGS. 4E–4D show rows of offset peaks, while alternatively FIG. 5B shows rows of aligned peaks 406. Either configuration may be used for any of the embodiments.

Figure 4F:
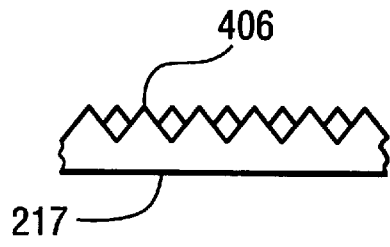
Figure 4G:
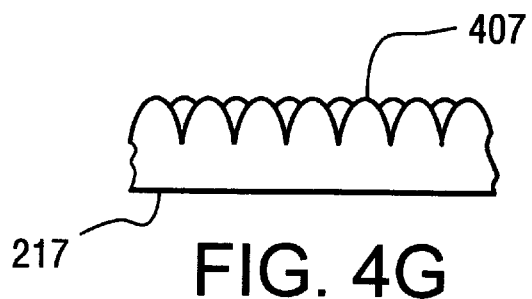

FIG. 4E shows a textured surface having a plurality of offset rows of peaks 405. The peaks may be relatively pointed or somewhat blunted. Each row may be offset from adjacent rows. FIG. 4F shows a textured surface having a plurality of offset rows of triangular or conical peaks 406. The peaks may be relatively pointed or somewhat blunted. FIG. 4G shows a textured surface 217 having a plurality offset rows of knobs or bumps 407.

The textured surface may be employed to minimize and decrease the friction and the capillary action-based attraction. A method for decreasing gel-to-support friction therefore includes providing a gel-contacting surface of a solid support with a plurality of projections (the textured surface 217), with the textured surface 217 reducing a contact area between the tank 200 and the gel 100. Preferably, the textured surface 217 provide on the solid support reduces the contact area to less than about twenty percent of a contact area provided by a flat surface. However, in an alternate embodiment, the texture may not lessen the contact area as much but yet still provide a benefit of a decreased friction and attraction. In an ideal case, the contact are may be less than 1% of the flat surface area.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A slab gel processing tank for treating an electrophoresis gel slab with a treating liquid, said tank comprising:
   a bottom;
   two substantially parallel end panels; and
   two substantially parallel side panels having substantially vertical lower portions and outwardly angled upper portions, said upper portions including a textured surface to minimize contact with said gel slab during a lowering movement of said gel into said tank;
   wherein said tank is dimensioned to contain said treating liquid and said electrophoresis gel slab.

2. The tank of claim 1, wherein said textured surface is formed of a plurality of ridges and troughs having a substantially circular cross-sectional shape.

3. The tank of claim 1, wherein said textured surface is formed of a plurality of ridges and troughs having a substantially sinusoidal cross-sectional shape.

4. The tank of claim 1, wherein said textured surface is formed of a plurality of ridges and troughs having a substantially triangular cross-sectional shape.

5. The tank of claim 1, wherein said textured surface is formed of a plurality of ridges and troughs having a substantially triangular cross-sectional shape and having squared-off peaks and valleys.

6. The tank of claim 1, wherein said textured surface is formed of a plurality of pointed peaks.

7. The tank of claim 1, wherein said textured surface is formed of a plurality of blunted peaks.

8. The tank of claim 1, wherein said textured surface is formed of a plurality of triangular peaks.

9. The tank of claim 1, wherein said textured surface is formed of a plurality of conical peaks.

10. The tank of claim 1, wherein said textured surface is formed of a plurality of knobs.

11. The tank of claim 1, wherein said tank further includes a fluid level sensor.

12. The tank of claim 1, wherein said tank further includes a drain and an inlet.

13. The tank of claim 1, wherein said lower portions of said side panels are transparent.

14. The tank of claim 1, wherein said two substantially parallel side panels are about one inch apart.

15. A slab gel processing tank for treating an electrophoresis gel slab with a treating liquid, said tank comprising:
   a bottom;

two substantially parallel end panels;

two substantially parallel transparent side panels having substantially vertical lower portions and outwardly angled upper portions, said upper portions including a textured surface with a plurality of alternating ridges and troughs, said ridges being spaced apart to minimize contact of said side panels with a gel slab during a lowering movement of said gel into said tank, said plurality of ridges and troughs having a substantially pyramidal cross-sectional shape;

a fluid level sensor for detecting a level of said heating liquid in said tank;

a drain; and an input;

wherein said tank is dimensioned to contain said treating liquid and said electrophoresis gel slab.

16. The tank of claim 15, wherein said two substantially parallel side panels are about one inch apart.

17. A method of supporting an electrophoresis gel slab and reducing sticking of said gel to a solid support, comprising the steps of:

providing a gel-contacting support surface of said solid support with a plurality of spaced apart projections; and positioning said gel slab on said support surface; wherein said plurality of projections touch said gel slab and said projection have a contact area less than the dimension of said support surface.

18. The method of claim 17, wherein said plurality of projections are provided by a textured surface formed of a plurality of ridges and troughs having a substantially circular cross-sectional shape.

19. The method of claim 17, wherein said plurality of projections are provided by a textured surface formed of a plurality of ridges and troughs having a substantially sinusoidal cross-sectional shape.

20. The method of claim 17, wherein said plurality of projections are provided by a textured surface formed of a plurality of ridges and troughs having a substantially triangular cross-sectional shape.

21. The method of claim 17, wherein said plurality of projections are provided by a textured surface formed of a plurality of ridges and troughs having a substantially triangular cross-sectional shape and having squared-off peaks and valleys.

22. The method of claim 17, wherein said plurality of projections are provided by a textured surface formed of a plurality of pointed peaks.

23. The method of claim 17, wherein said plurality of projections are provided by a textured surface formed of a plurality of blunted peaks.

24. The method of claim 17, wherein said plurality of projections are provided by a textured surface formed of a plurality of triangular peaks.

25. The method of claim 17, wherein said plurality of projections are provided by a textured surface formed of a plurality of conical peaks.

26. The method of claim 17, wherein said plurality of projections are provided by a textured surface formed of a plurality of knobs.

27. The method of claim 17, wherein said plurality of projections renders said actual contact area between said gel and said support to be less than about twenty percent of an overlap area over which said gel and said solid support overlap.

28. A slab gel processing tank for treating an electrophoresis gel slab with a treating liquid, said tank comprising:

two side panels spaced apart to define an inner space of said tank, said space being dimensioned to contain said treating liquid and said gel slab, said side panels being spaced apart a distance to receive said gel slab therebetween substantially without said gel slab contacting said side panels;

a plurality of spaced apart projections extending from said side panels a distance to prevent sticking of said gel slab to said side panels; and a treating liquid contained in said inner space.

29. The tank of claim 28, wherein said projections are spaced apart to define a recess between adjacent projections, and wherein said projections are spaced apart a distance to prevent said gel slab from contacting said recess.

30. The tank of claim 29, wherein each of said side panels include a lower portion and an upper portion, said upper portion being oriented at an incline with respect to said lower portion sufficient to guide said gel slab into said treating liquid, and wherein said projections are formed on said upper portion.

31. A method of treating an electrophoresis gel slab with a treating liquid, said method comprising:

providing a treatment tank containing said treating liquid and having two spaced apart side panels, said side panels being spaced apart a distance to receive said gel slab therebetween substantially without said gel slab contacting said side panels, said side panels further having a plurality of spaced apart projections extending from said side panels a distance to prevent said gel slab from sticking to said side panels, and positioning said gel slab in said treating liquid substantially without said gel slab sticking to said side panels.

32. The method of claim 31, wherein each of said side panels include a lower portion and an upper portion, said upper portion having said projections extending therefrom, said method comprising positioning said gel slab in said tank whereby said gel slab contacts said upper portion and slides over said projections into said treating liquid without damaging said gel slab.

* * * * *

UNITED STATES PATENT AND TRADEMARK OFFICE
CERTIFICATE OF CORRECTION

PATENT NO. : 6,298,874 B1
DATED : October 9, 2001
INVENTOR(S) : Anderson et al.

It is certified that error appears in the above-identified patent and that said Letters Patent is hereby corrected as shown below:

Column 1,
Line 7, insert:
-- This invention was made with United States Government Support under cooperative agreement number 70NANB5H1075 awarded by the National Institutes of Standards and Technology. --

Signed and Sealed this

Ninth Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,298,874 B1
DATED : October 9, 2001
INVENTOR(S) : Anderson et al.

Page 1 of 1

It is certified that error appears in the above-identified patent and that said Letters Patent is hereby corrected as shown below:

Column 1,
Line 7, insert -- This invention was made with United States Government support under cooperative agreement number 70NANB5H1075 awarded by the National Institute of Standards and Technology. The government has certain rights in the invention. --.

Signed and Sealed this

Twenty-fifth Day of October, 2005

JON W. DUDAS
*Director of the United States Patent and Trademark Office*